United States Patent
Clarke

[19]

[11] Patent Number: 5,946,920
[45] Date of Patent: Sep. 7, 1999

[54] METHOD AND APPARATUS FOR SUPPLYING LIQUID CRYOGEN

[75] Inventor: Brian K. R. Clarke, Oakwood, United Kingdom

[73] Assignee: Spembly Cryosurgery Limited, Hampshire, United Kingdom

[21] Appl. No.: 08/930,461

[22] PCT Filed: Apr. 1, 1996

[86] PCT No.: PCT/GB96/00787

§ 371 Date: Apr. 13, 1998

§ 102(e) Date: Apr. 13, 1998

[87] PCT Pub. No.: WO96/30816

PCT Pub. Date: Oct. 3, 1996

[30] Foreign Application Priority Data

Mar. 31, 1995 [GB] United Kingdom ............... 9506652

[51] Int. Cl.[6] ........................... F17C 7/02; F25B 19/02
[52] U.S. Cl. ........................................ 62/50.1; 62/51.2
[58] Field of Search ................................ 62/48.3, 50.2, 62/51.1, 51.2, 50.1

[56] References Cited

U.S. PATENT DOCUMENTS

| | | | |
|---|---|---|---|
| 2,908,145 | 10/1959 | Haumann | 62/48.3 |
| 4,116,199 | 9/1978 | Bryne . | |
| 4,175,395 | 11/1979 | Prost et al. | 62/50.2 |
| 4,275,734 | 6/1981 | Mitchiner . | |
| 4,278,090 | 7/1981 | Van Gerven | 62/51.2 X |
| 4,296,610 | 10/1981 | Davis . | |
| 4,750,338 | 6/1988 | Hingst | 62/51.2 |
| 4,946,460 | 8/1990 | Merry et al. . | |
| 5,172,558 | 12/1992 | Wassibauer et al. . | |
| 5,327,732 | 7/1994 | De Almeida . | |
| 5,334,181 | 8/1994 | Rubinsky . | |
| 5,564,278 | 10/1996 | Gallivan | 62/51.2 |
| 5,571,231 | 11/1996 | Lee | 62/50.4 X |
| 5,577,387 | 11/1996 | Maytal | 62/51.2 |
| 5,761,911 | 6/1998 | Jurcik et al. | 62/50.2 |

Primary Examiner—Christopher B. Kilner
Attorney, Agent, or Firm—Renner, Otto, Boisselle & Sklar, P.L.L.

[57] ABSTRACT

A method and apparatus are described for controlling the rate of supply of a liquid cryogen, for example, for cryosurgical use. The flow rate of the liquid cryogen is controlled by controlling variably the pressure propellant gas acting directly or indirectly on the liquid cryogen. A means for controlling the propellant gas pressure may comprise a source of pressurised propellant gas, and control valve means coupled between the source and the liquid cryogen reservoir chamber for controlling the pressure supplied to the reservoir chamber. A plurality of reservoir chambers may be driven by a common pressure source. When the pressure source is a pressure raising system, the cryogen reservoir chambers may be contained within the vessel of the pressure raising system. A feedback control arrangement is also described for controlling the cryogen flow rate in response to a measured characteristic associated with, or affected by, the cryogen flow rate. For example, in cryosurgery, the measured characteristic may be temperature as measured by a temperature probe.

27 Claims, 5 Drawing Sheets

METHOD AND APPARATUS FOR SUPPLYING LIQUID CRYOGEN

This invention relates to a method and apparatus for controlling the rate of supply of a liquid cryogen. The invention is particularly suitable for use in the supply of liquid cryogen to cryosurgical apparatus, but it is not limited exclusively to this.

Figure 1:
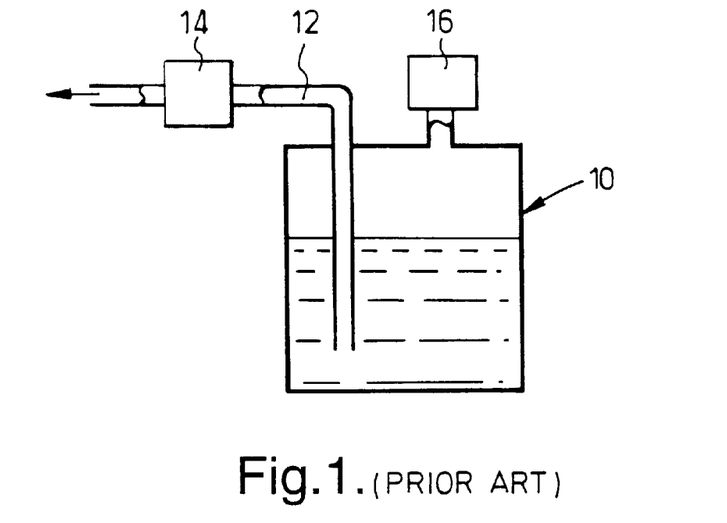

FIG. 1 illustrates schematically a conventional type of controllable cryogen supply. The liquid cryogen, typically Nitrogen, is contained in a vacuum insulated pressure vessel 10 which is generally sealed except for an outlet tube 12 extending below the surface of the liquid. The extreme volatility of the liquid results in the liquid boiling in the vessel 10 (or in a separate heat exchange circuit communicating with the vessel), which in turn causes a build up of pressure above the liquid surface. This gaseous pressure acts as a propellant to drive the liquid out through the tube 12.

A control valve 14 is fitted in the outlet tube 12 downstream of the vessel 10 for regulating the output flow rate as desired. In order to ensure that the pressure of the Nitrogen gas in the vessel does not reach too high a level, a pressure safety valve, or relief valve, 16 coupled to the vessel 10 opens automatically at a predetermined pressure to allow excess pressure to escape.

The control valve 14 is needed in this design so that the output rate can be controlled. In the field of cryosurgery, the flow rate determines the magnitude of the freezing effect. Not only does this vary depending on particular surgical operation to be carried out, but it is often necessary to increase or decrease the magnitude of the freezing effect at different times as part of the cryosurgical treatment.

However, there are significant problems associated with placing a control valve 14 in the flow line of the liquid cryogen. Firstly, the valve has to be designed to operate at the extremely low temperature of the liquid cryogen without risk of the valve freezing open or closed. Typically, the operating temperature would be less than −196° C. for liquid Nitrogen. The cost of many such valves is prohibitively expensive, and only two types of valve are in general use today. These are: (i) a manually operable tap which is not suitable for automated operation by electronic control; and (ii) an electromagnetic on/off valve, which can only be controlled to regulate the flow rate by being switched repeatedly between the on (open) and off (closed) states.

Not only are cryogen valves expensive, they also reduce the efficiency of, and introduce unpredictability in the performance of cryosurgical instruments. The valve mechanism represents a considerable thermal mass in contact with the liquid cryogen flowing through the valve, causing undesirable heat gain (i.e. the thermal mass acts as a sink to the cooling capacity of the liquid cryogen). Heat gain is a problem associated with both types of valve discussed above, but it is particularly associated with the electromagnetic valve because heat is also generated by the flow of electric current in the valve mechanism A further problem associated with the electromagnetic valve is that gas bubbles are produced in the liquid cryogen. The gas bubbles are caused by contact of the cryogen with the electrically driven shutter of the valve mechanism when the valve is closed. Upon such contact, localised boiling of the liquid occurs, creating a gas bubble. The valve has to be driven repeatedly to control the liquid flow rate, and bubbles are thus created continuously in the stream of liquid. Furthermore, when low flow rates are required, the valve has to held shut for a considerably longer period than it is open, which results in much larger gas bubbles.

Particularly in the field of cryosurgery, uniform laminar flow of cryogen in the supply tube is desired, as this enables better phase separation in an instrument such as a cryogenic probe, and enables efficient nuclear boiling to be established and maintained. However, the gas bubbles and the turbulence created by the intermittent operation of the electromagnetic valve disrupt the desired laminar flow, and reduce the effectiveness and controllability of cryosurgical instruments.

Reference is also made to U.S. Pat. No. 4,275,734, which describes a method and apparatus are described for controlling the rate of supply of a liquid cryogen, for example, for cryosurgical use. The flow rate of the liquid cryogen is controlled by controlling variably the pressure propellant gas acting directly or indirectly on the liquid cryogen. A means for controlling the propellant gas pressure may comprise a source of pressurised propellant gas, and control valve means coupled between the source and the liquid cryogen reservoir chamber for controlling the pressure supplied to the reservoir chamber. A plurality of reservoir chambers may be driven by a common pressure source. When the pressure source is a pressure raising system, the cryogen reservoir chambers may be contained within the vessel of the pressure raising system.

The present invention has been devised bearing in mind the aforementioned problems appreciated by the applicant.

In contrast to the prior art technique of regulating the flow rate of liquid cryogen downstream of the cryogen supply, one aspect of the present invention is to control the flow rate by controlling variably the pressure of propellant gas acting directly or indirectly on the liquid cryogen.

Such a technique offers immediate advantages over the prior art discussed above, in moving the means by which the flow rate is controlled, away from a critical position in the flow path of the liquid cryogen. Therefore, the conventional downstream valve can be omitted, and the problems associated with such a valve can be almost completely avoided.

One particular advantage is that, by omitting the downstream valve, the thermal mass in contact with the liquid cryogen flowing in the tube is very significantly reduced.

A further particular advantage is that the delivery pressure of the liquid cryogen can be controlled reliably, and the invention can accommodate cryogen delivery at low pressure (i.e. slightly above atmospheric pressure) as well as at high pressure. This is a particular advantage for certain types of cryosurgical instruments to which cryogen needs to be fed at a low delivery pressure.

Another particular advantage is that a relatively inexpensive type of valve can be used to control the gaseous pressure, because the gas is not at cryogenic temperature. Whereas electronically controlled, variable throughput valves are not economically available for handling liquid cryogen, such valves are available for controlling gases. By using such a valve to adjust the gaseous pressure anywhere within a predetermined range, the liquid flow rate can be varied under electronic control to produce a smooth, uninterrupted supply of liquid cryogen, free of gas bubbles, even at low flow rates.

Preferably, the valve operates under the control of an electronic control circuit, for example, a computerised control circuit.

The propellant gas may be produced from the reservoir of liquid cryogen to be supplied. For example, the pressure can be regulated by a control valve which simply vents the gas pressure from the reservoir controllably. Such a technique might not be ideal in all situations, because the continuous boiling of the liquid cryogen, and the controlled venting to achieve a desired liquid flow rate, inevitably results in wastage. Furthermore, the response of this system will always lag behind any commanded increase in the flow rate, because the system has to rely on the natural boiling of the liquid to build up propellant pressure.

Therefore, a preferred feature of the invention is that the propellant gas is supplied from a pressure source, or pressure raiser, external to the reservoir of the liquid cryogen being supplied. The reservoir for the liquid cryogen can then be designed for optimum thermal isolation to prevent undesired boiling in the reservoir itself. Likewise, the external pressure source or pressure raiser can be designed to provide changes in gas pressure on command.

The pressure of the propellant gas can be varied by a pressure control valve coupled between the liquid cryogen reservoir vessel and the external pressure source or pressure raiser.

Preferably, a head of positive pressure of gas is maintained in a container upstream of the control valve. The source might, for example, be a replaceable canister of pressurised gas/liquid cryogen. Alternatively, a separate pressure raiser can be used to boil liquid cryogen outside the reservoir vessel. By maintaining a positive head of pressure, a reserve of pressure is always available so that the flow rate of the cryogen can be increased on command.

In a preferred arrangement, a number of individually controllable cryogen reservoir vessels are provided to enable a plurality of different cryosurgical instruments to be fed from the same system. Conveniently, a common source of pressurised propellant gas is used, and this is coupled to each cryogen reservoir vessel by a respective, independently controllable pressure valve, such that the cryogen flow from each reservoir vessel can set independently of the others.

Preferably, the cryogen reservoir vessels are contained together within a larger vessel of further cryogen liquid. This provides improved thermal insulation of the reservoirs from the ambient surroundings. Conveniently, the larger vessel can be a pressure rasing vessel used to produce gas under pressure to act as the propellant for the individual cryogen reservoirs.

It is preferred, although not essential, that the propellant gas be the same substance as the liquid cryogen. This can avoid problems of impurities in the liquid cryogen, and reduces the need for thorough cleaning each time the supply system is used.

A further aspect of the invention is to measure a temperature using a temperature probe distinct from, and spaced from, a cryosurgical device, and to control the rate of flow of the liquid cryogen to the cryosurgical device by electronic control means responsive to the measured characteristic, whereby the cooling effect, for example, in tissue can be measured and controlled.

The temperature of body tissue may be measured at one or more predetermined distances from the tip of the cryosurgical probe. Such an arrangement would, for example, enable a desired temperature profile or gradient to be established in the tissue around the probe.

It might be desired in a cryosurgical procedure to control the rate at which frozen tissue is allowed to unfreeze, such that the unfreezing is slower than the natural unfreezing by body heat. To do this, the rate of flow of cryogen is controlled at a deliberately low rate which is insufficient to maintain the current low temperature in the body tissue, but is sufficient to slow the rate of heating. With this aspect of the present invention, the temperature in the tissue around the probe can be measured, and the flow rate controlled in response to the measured temperature to achieve a desired change in temperature over time.

The second aspect of the invention may be used independently of the first aspect, but advantageous results can be achieved by combining these aspects. Particularly in the field of cryosurgery, the greater control and predictability provided by the first aspect of the invention enables more accurate and stable "feedback" control used in the second aspect.

According to the invention there is also provided a method of controlling the rate of supply of a liquid cryogen to cryosurgical apparatus, in which the flow of the liquid is effected by the pressure of a gas acting directly or indirectly on the liquid, the method comprising controlling the pressure of the gas whereby to control the rate of flow of the liquid.

According to the invention there is further provided apparatus for supplying a liquid cryogen to cryosurgical apparatus, the apparatus comprising means for supplying the liquid cryogen to the cryosurgical apparatus and pressure controlling means whereby the rate of flow of the cryogen to the cryosurgical apparatus can be varied, the pressure controlling means comprising means for providing a supply of gas in communication with the liquid cryogen and means for varying the pressure of said gas, whereby to vary the rate of flow of liquid cryogen to the cryosurgical apparatus.

Embodiments of the invention are now described, by way of example only, with reference to the accompanying drawings, in which.

A first basic embodiment is described with reference to FIG. 2 to illustrate the principle of operation in the invention. The liquid cryogen, typically liquid Nitrogen, is stored in a twin-walled stainless steel reservoir vessel 20. The region 22 between the walls is evacuated for the purpose of heat insulation. Projecting from within the vessel are three conduits 24, 26 and 28. Two of the conduits 24 and 26 extend towards the bottom of the vessel such that their open ends lie beneath the surface of the liquid cryogen, and the third conduit 28 extends only a short way into the vessel 20 such that its open end is above the surface of the liquid.

The first conduit 24 serves as a filling tube to enable the liquid cryogen to be supplied to the vessel 20. Normally, this conduit is sealed by a valve 30. The second conduit 26 serves as a delivery tube through which the liquid cryogen is delivered, in use, to a cryosurgical instrument (not shown). The conduit 26 is unregulated in that no flow control valve is fitted between the vessel 22 and the delivery end of the conduit.

The third conduit 28 serves as an input for propellant gas under pressure from a pressure source or pressure raising system (designated schematically by 32) external to the reservoir vessel 20. Typically, the gas will be the cryogen in the gaseous phase (for example, Nitrogen gas), but this is not essential. The third conduit is coupled to the source 32 through a three port valve 34, the third port of which serves as a vent 35 to the atmosphere, and through a pressure control valve 36 upstream of the three port valve 34. A pressure limiting valve 38 may also be provided to limit the maximum pressure of gas from the source, for example, to about 60 p.s.i. (approximately 420 kPa).

The control valve 36 enables the pressure of gas within the vessel 20 to be controlled variably up to the maximum pressure allowed by the pressure limiting valve 38. In use, the control valve 36 is adjusted to pressurise the vessel 20 with propellant gas at a pressure which drives the liquid cryogen through the delivery conduit 24 at a desired flow rate. The flow rate can be increased, or decreased, simply by increasing, or decreasing, the gas pressure.

In such a system, the control of the flow rate is effected by controlling the pressure of propellant gas which is not itself at a cryogenic temperature. No valves are needed in the flow path of the liquid cryogen. Smooth flow can be achieved at low flow rates, and the valve can be a conventional electrically controllable gas handling valve.

To stop the flow of liquid cryogen from the vessel, the three port valve 34 is operated to block the supply of further gas from the source 32, and to vent the third conduit 28 to atmospheric pressure through the vent port 35. This results in the immediate loss of positive pressure within the vessel, thereby halting the delivery of liquid cryogen. The rapid venting of the pressurised gas can also cause the momentary occurrence of mild negative pressure in the vessel, thereby drawing back slightly the liquid cryogen in the delivery conduit 26. This can help prevent seepage which might otherwise occur at the delivery end of the conduit 26 once the flow has stopped.

The source 32 of propellant gas may, for example, be a pressurised canister of gas which can be replaced once empty. Alternatively, a pressure raising system may be used to develop gas under pressure from liquid cryogen. Any suitable form of pressure raising system can be used, such as a coiled heat exchanging conduit communicating with ambient temperature, or an electrical heater. The supply of liquid cryogen for use in the pressure raising system may either be drawn from the vessel 20 (for example, by a supply conduit shown schematically at 40 in FIG. 2), or from a separate reservoir of the liquid, as in the pressure raising system illustrated in FIG. 3.

Figure 3:
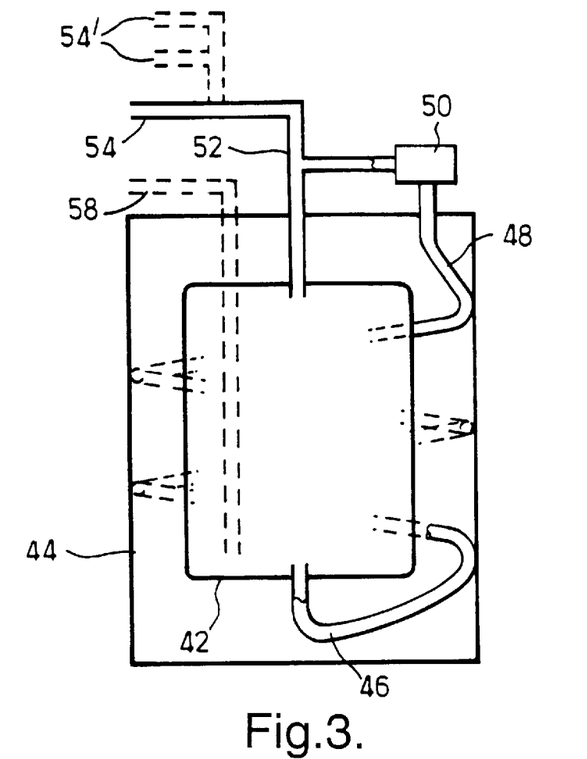
FIG. 3 is a schematic illustration of a pressure raising vessel for use in the system in FIG. 2.

Referring to FIG. 3, that pressure raising system includes an inner vessel 42 containing liquid cryogen, and an outer vessel 44 surrounding the inner vessel 42 and separated therefrom by a vacuum for the purpose of heat insulation. A heat exchange conduit 46 leads from the lower end of the inner vessel 44 and is coiled helically in contact with the inner surface of the outer vessel 44 to enable liquid cryogen in the coiled conduit to absorb heat from the surrounding environment. Both vessels 42 and 42 may be of stainless steel, and the coiled portion of the conduit 46 in contact with the outer vessel may be soldered to the outer vessel.

The upper end 48 of the conduit 46 projects through the outer vessel 44 and is coupled through a pressure control valve 50 to a T-junction 52. One branch of the T-junction 52 feeds back through the outer vessel 44 into the inner vessel 42 above the surface of the liquid cryogen, and the other branch provides an output conduit 54 for delivering the propellant gas under pressure. The output conduit 54 is coupled through the pressure control valve 36 and the three port valve 34 (see FIG. 2) which regulate the amount of propellant pressure fed to the cryogen reservoir 20.

In use, liquid cryogen drawn from the bottom of the inner vessel 42 into the conduit 46 boils in the coiled portion, and the gas is fed back through the pressure control valve 50 to the inner vessel 42, so that a head of pressure develops in the vessel 42. The pressure control valve 50 takes the place of the valve 38 in FIG. 3 and limits the maximum pressure of gas exiting the heat exchange conduit, and thereby limits the maximum head of pressure developed in the vessel 42. When the maximum pressure is achieved, the system is in equilibrium, and no further liquid cryogen is drawn into the heat exchange conduit 46. When propellant gas is drawn away through the delivery conduit 54, and the head of pressure in the vessel 42 begins to fall below the maximum, replacement gas flows into the vessel from the heat exchange conduit 46 until the maximum gas pressure is restored.

Such a system is entirely self-regulating and improves efficiency by preventing the build-up of excess gas pressure, which would otherwise need to be vented.

Figure 2:
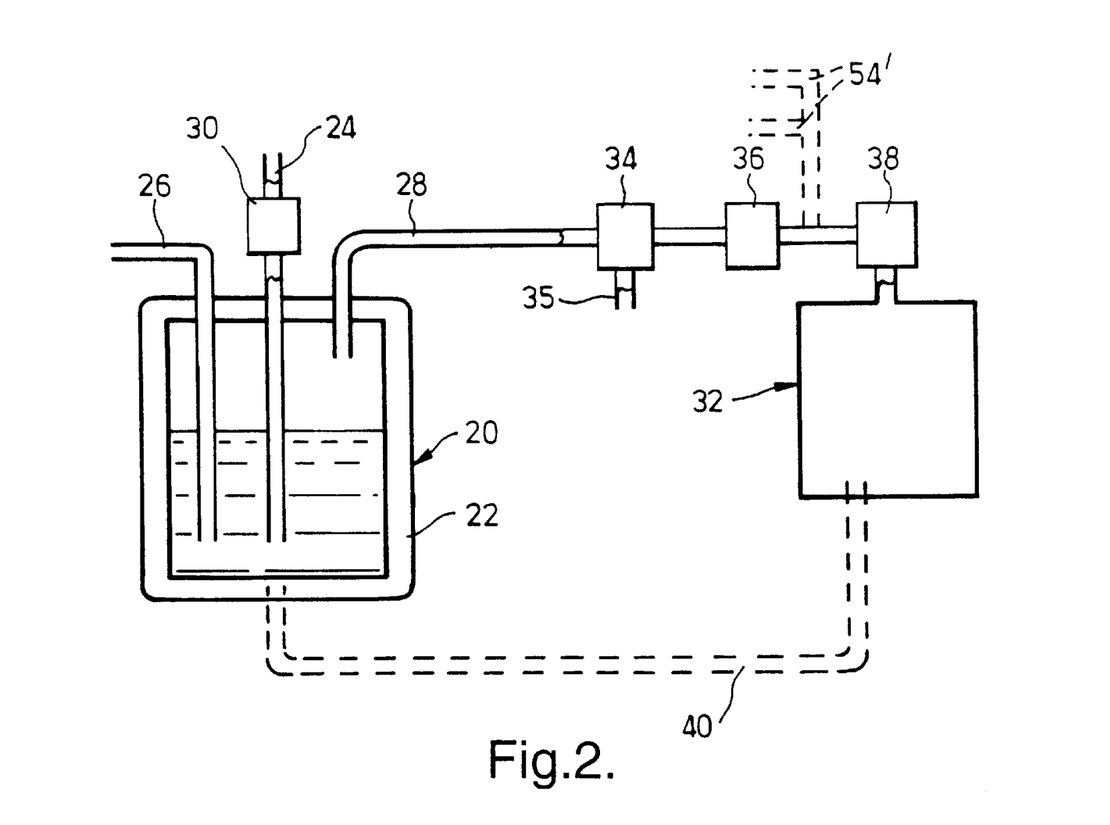
FIG. 2 is a schematic illustration of a first system in accordance with the present invention.

As illustrated in phantom in FIGS. 2 and 3 at 54', the delivery tube 54 may be branched to deliver pressurised propellant for driving a number of different liquid cryogen reservoirs in parallel. In this case, a separate pressure control valve 36 and three port valve 34 would be provided for each liquid cryogen reservoir downstream of the branch to enable the cryogen flow rate from each reservoir to be controlled individually.

The system in FIG. 3 has been described as providing a source of propellant gas for driving one or more separate cryogen reservoirs. Generally, the maximum pressure control valve 50 would be a fixed pressure valve, or pre-set to a pre-determined pressure. However, if a variable type maximum pressure valve is used, this would provide a further technique for controlling variably the pressure of propellant gas in the vessel.

In a modified embodiment using a variable type pressure control valve 50, the vessel 42 can be used as a combined pressure raising vessel and reservoir of liquid cryogen to be supplied. By providing an outlet tube 58 (shown in phantom in FIG. 3) similar to the conduit 24 in FIG. 2, liquid cryogen can be delivered at a desired flow rate which is fully controllable by the valve 50 in the heat exchange conduit 46. In such case, the propellant gas delivery conduit 54 would not be needed.

Figure 4:
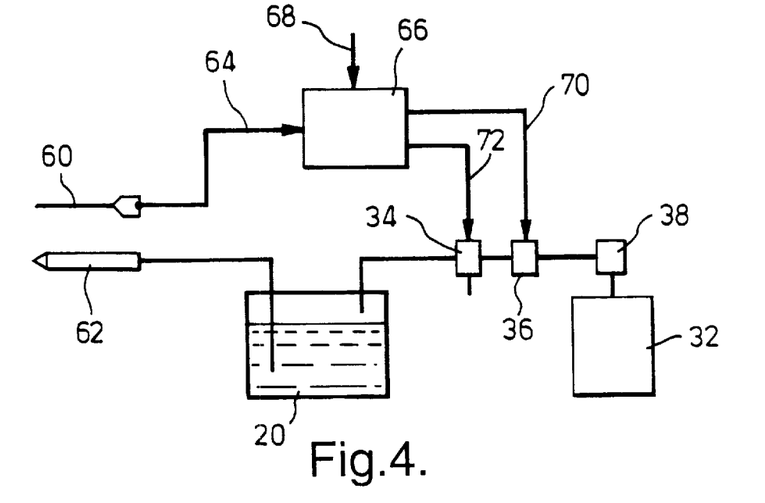
FIG. 4 is a schematic diagram illustrating control of the system of FIG. 2.

FIG. 4 illustrates a feedback arrangement for controlling the flow rate in the system of FIG. 2. A temperature sensing probe 60 is inserted into body tissue with a cryogen probe 62 fed by the cryogen reservoir 20. The temperature probe 60 serves to measure the temperature of the tissue at a predetermined distance from the tip of the cryogen probe 62. The output from the temperature probe is provided to a first input 64 of an electronic control circuit 66 which, in this embodiment, includes a programmed computer processor. Control information, representing the desired temperature, is also provided to the circuit 66 via a second input 68. The control circuit 66 controls the flow rate of the cryogen by means of a first output line 70 coupled to the flow control valve 36, and a second output line 72 coupled to the three port valve 34.

In operation, the control circuit 66 monitors the difference between the desired temperature and the measured temperature, and calculates any necessary correction to the cryogen supply rate to maintain the desired temperature. For example, if the measured temperature is above the desired temperature (ie. too hot), then the control circuit 66 calculates an increase in the cryogen supply rate to increase the cooling effect of the probe. Likewise, if the measured temperature is below the desired temperature (ie. too cold), the control circuit 66 calculates a decrease in the cryogen supply rate to lessen the cooling effect.

The control information may represent a static desired temperature, or it may represent a temperature which varies over time, for example, a controlled rise from frozen to normal body temperature. The control information may be inputted manually, or it may be pre-stored.

Although not shown in FIG. 4, additional temperature probes may be provided so that the temperature of the body tissue can be monitored at different points simultaneously. Such additional probes would be coupled to the control circuit 66 as additional inputs for use in the feedback control system.

Figure 5:
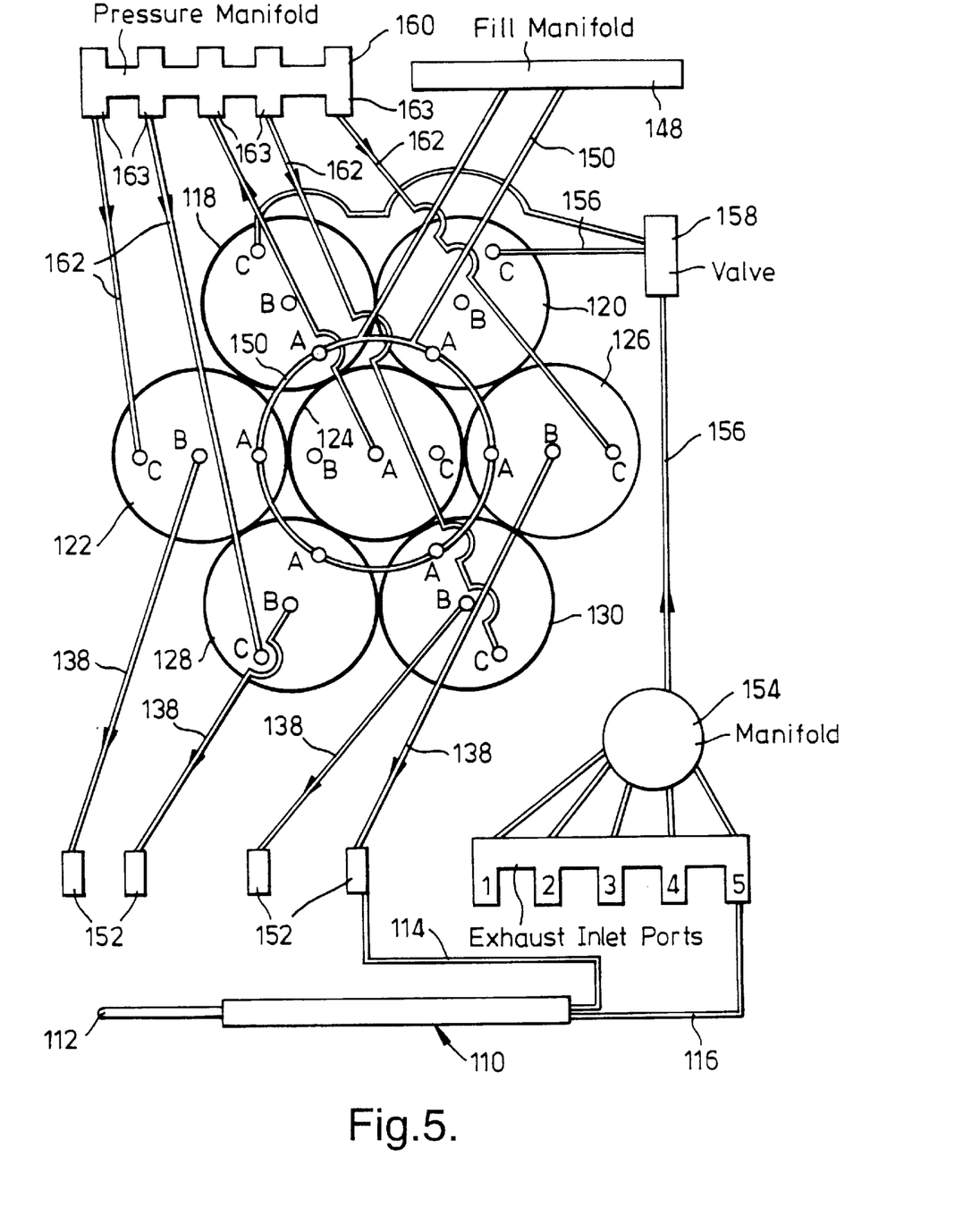
FIG. 5 is a schematic illustration of a second embodiment of the invention, for the supply of liquid Nitrogen to a cryosurgical probe.

Referring now to FIG. 5, there is shown a second system for the supply of liquid nitrogen for the purposes of cooling up to four cryosurgical instruments. The drawing shows one such instrument in the form of probe 110 for surgical use. The probe 110 has a body including a hollow tip region 112 which is cooled to the required operating temperature by the supply thereto of liquid Nitrogen. The liquid evaporates in the tip region 112, thereby cooling bodily tissues in contact therewith. Excess liquid Nitrogen, together with the resultant Nitrogen gas, returns through the probe body to an exhaust. A probe of this general type is known. In the system illustrated, liquid Nitrogen is supplied to the probe via a suitable supply line 114, and exhaust Nitrogen leaves the probe via a suitable exhaust line 116.

The liquid Nitrogen supply arrangement generally comprises seven substantially cylindrical vessels 118, 120, 122, 124, 126, 128, 130, which may be made of stainless steel. These vessels are contained within a larger cylindrical stainless steel outer vessel (not shown) which is substantively evacuated, for insulation purposes. The arrangement is such that the vessel 124 is located substantially along the longitudinal axis of the outer vessel, with the vessels 118, 120, 122, 124, 126, 128 and 130 located around the vessel 124.

Each of the vessels 118, 120, 122, 124, 126, 128, 130 is provided with three ports A, B, C.

Figure 6:
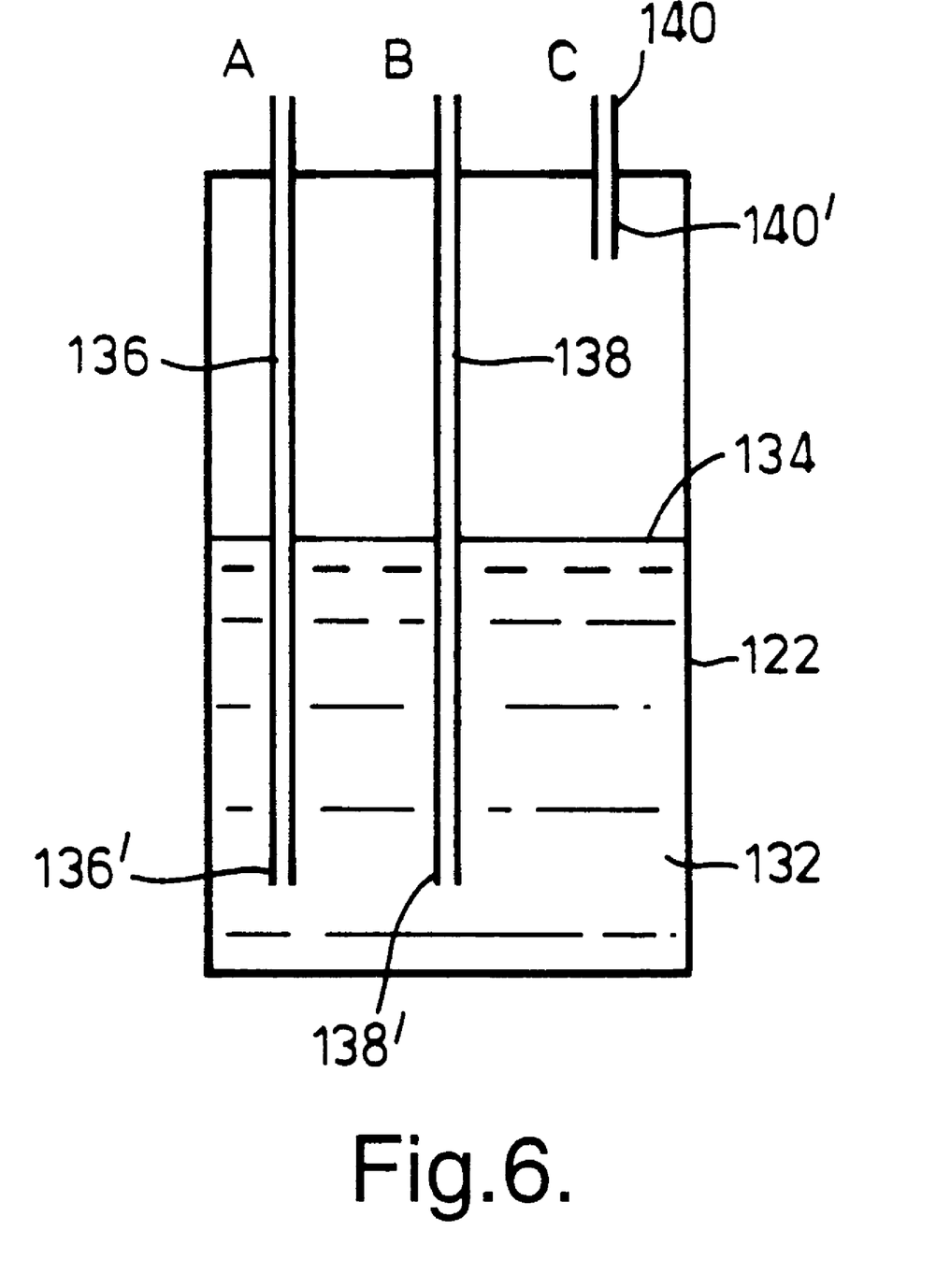
FIG. 6 is a diagrammatic side view of a liquid Nitrogen vessel of the system of FIG. 5.

FIG. 6 shows a diagrammatic side view of the vessel 122, which is similar to that described above in relation to FIG. 3. Vessels 126, 128 and 130 are also similar. FIG. 6 shows the vessel 122 part filled with liquid Nitrogen 132 under pressure, to a level indicated at 134. Each of the ports A, B, C is provided with a pipe 136, 138, 140 respectively, which passes from inside the vessel 122 through the respective port to the outside of the vessel. Each pipe is sealed within the respective port. As will be seen from FIG. 6, the pipes 136 and 138 extend substantially the entire length of the vessel 122, in particular so that a lower end 136', 138', of each pipe is below the liquid level 134. The pipe 140 only extends a short way into the vessel 122 from the port C, so that an end 140' thereof is located above the liquid level 134. Respective ends of pipes 136, 138, 140 projecting externally of vessel 122 are appropriately connected within the system as will be further described hereinafter. Each of the cylinders 122, 126, 128 and 130 acts within the system as a reservoir of liquid Nitrogen for supply to a cryosurgical instrument.

The central vessel 124 enables the control of pressure within the system, and in particular within each of the reservoirs 122, 126, 128 and 130. The vessel 124 contains liquid and gaseous Nitrogen under pressure. In a similar fashion to that described in relation to FIG. 3, a pipe (not shown) leaves the vessel 124 via a port, and returns to the vessel 124 through a further port located beneath the level 134 of liquid Nitrogen. An intervening portion of the pipe is helically coiled around the inner surface of the outer vessel in such a manner as to permit heat exchange between contents of the pipe and the ambient atmosphere surrounding the outer vessel.

The vessels 118 and 120 are similar in construction to the vessel 122 shown in FIG. 6, but act as receiving vessels for exhaust products of the probe 110, which are supplied to a pipe located within port C. The port B of tanks 118, 120 is arranged to provide a vent to atmosphere.

Referring again to FIG. 5, there is provided in the system a filling manifold 148 connected by means not shown to a supply of liquid Nitrogen. The manifold 148 effectively provides a ring circuit 150 which connects to pipe 136 of each of the reservoir vessels 122, 126, 128, 130. Appropriate valve arrangements are provided in association with the manifold 148 and the circuit 150 so that liquid Nitrogen may be supplied to the reservoir vessels as required to raise the level of the liquid Nitrogen within each vessel to the level 134. Whilst filling of a vessel is taking place, the pipe 140 is opened to atmosphere by means of an appropriate valve arrangement (not shown) to allow gas to escape from the vessel.

Liquid Nitrogen is supplied from each reservoir vessel 122, 126, 128, 130 by means of the pipe 138. Each pipe 138 is extended from the port B by means of a suitable line to a respective outlet port 152 of the system. In the system shown in the drawing, there are provided four outlets 152, only one of which is in use. The outlet 152 is connected in a suitable manner to cryogen supply line 114 to the probe 110.

As previously indicated, exhaust products from the probe 110 pass out of the probe via a line 116, which passes to one of four exhaust inlet ports 11, 12, 13, 14, 15, each of which in turn connects to an exhaust manifold 154. A line 156 connects the manifold 154 by means of a valve 158 to the port C of each of the receiving tanks 118, 120. Nitrogen gas from the exhaust vents to atmosphere through the port B. Liquid nitrogen can drop into the vessels 118, 120.

The pressure in each of the reservoir vessels is generated and controlled by means of pressure raising vessel 124. Briefly, Nitrogen gas pressure from within the vessel 134 is supplied via suitable connections from port A to a pressure manifold 160 (FIG. 5), which in turn provides four outlets each connected via an appropriate line 162 to one of the reservoir vessels 122, 126, 128, and 130. The line 162 connects into the respective vessel valve the pipe 140, and a suitable valve arrangement. This gas pressure acting on the liquid Nitrogen 132 within the reservoir tank causes the liquid Nitrogen to be supplied via the pipe 138 and intermediate connections to the probe 10. Suitable valve arrangements 163 are provided between the manifold 160 and each reservoir tank for regulating the pressure provided to the tank and therefore the rate of the flow of liquid Nitrogen from the tank to the probe.

Pressure is generated within the vessel 124 by the boiling of liquid Nitrogen therein. The liquid passes out of the vessel through the helically coiled pipe. As previously described, this pipe permits heat exchange between the liquid Nitrogen contained therein and the ambient atmosphere outside the outer vessel. Accordingly, the liquid Nitrogen boils to provide a head of pressure within the vessel 134. When the port A is open, pressure is released form the vessel 124 to the pressure manifold 160. This automatically permits liquid to pass into the coiled pipe, thus allowing more liquid to boil and generate gas. In this way, the pressure of the head of gas is restored. A pressure relief valve is provided and is set to a pressure at a suitable level above the operating pressure of the system.

Figure 7:
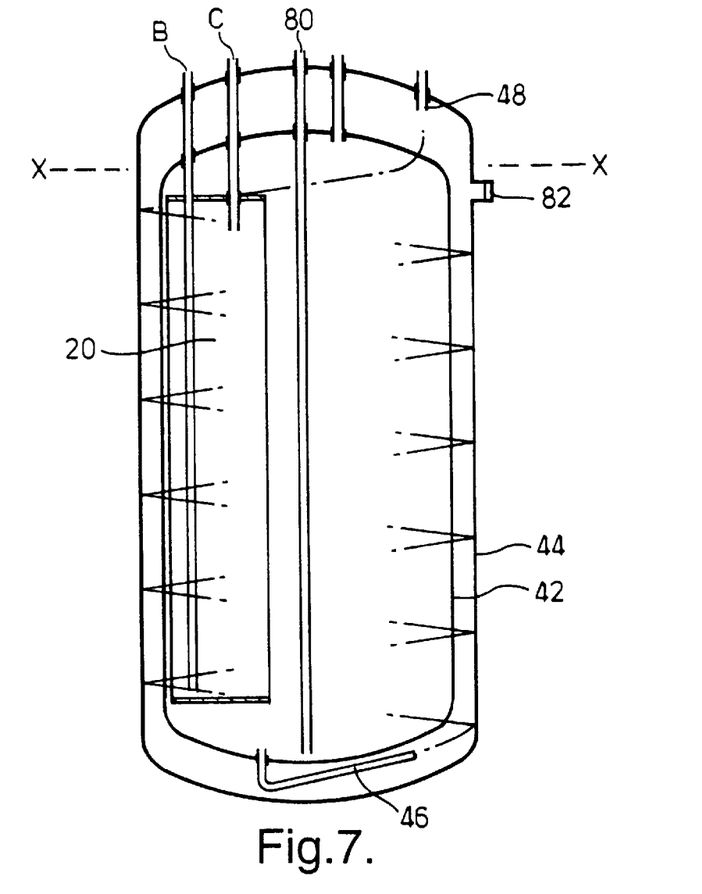
FIG. 7 is schematic vertical-section through a third embodiment of the present invention.
Figure 8:
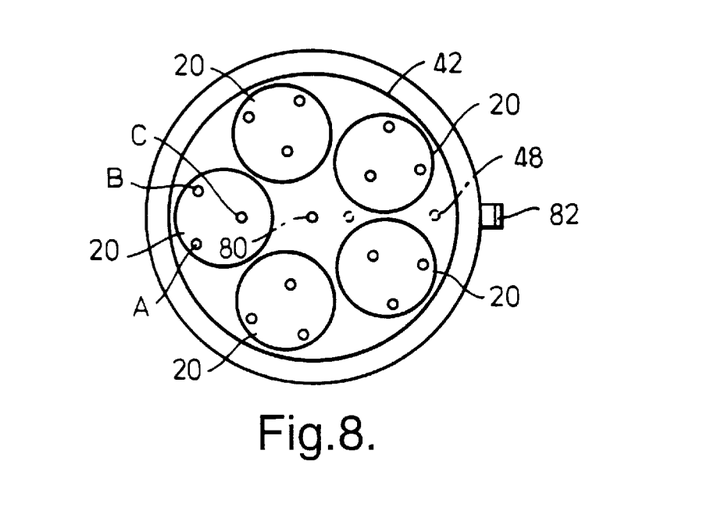
FIG. 8 is horizontal section along the line X—X in FIG. 7.

FIGS. 7 and 8 illustrate a modified design which is similar in principle to the embodiments described above in relation to FIGS. 2–3 and 5–6. The main difference is that a number of liquid cryogen supply reservoirs 20 are arranged as chambers within a surrounding pressure raising vessel 42 also containing liquid cryogen for the generation of propellant gas. As best seen in FIG. 8, five reservoir chambers 20 are illustrated on a pitch circle diameter within the pressure raising vessel 42. Each reservoir has a filling conduit/port A, a liquid cryogen output conduit/port B and a propellant input conduit/port C which correspond to the conduits described previously. The weight of each reservoir is supported by the conduits which project through the pressure raising vessel 42 and the outer evacuated vessel 44. The heat exchange conduit 46 extends from the bottom of the vessel 42 and is wound helically around the inner surface of the outer vessel as described hereinbefore. A fill conduit 80 extends into the pressure raising vessel 42 at the top, and extends towards the bottom, to enable the pressure rasing vessel 42 to be filled with nitrogen before use. The outer vessel 44 includes a port 82 for connection to a vacuum pump (not shown) to evacuate the region between the outer vessel 44 and the pressure raising vessel 42.

With this design, the liquid cryogen reservoir vessels 20 are surrounded by the liquid cryogen in the pressure rasing vessel 42, as well as by the vacuum "jacket". This further insulates the reservoir vessels 20 from external ambient temperature.

If desired, one or more of the reservoir vessels 20 may be used as an exhaust collection vessel, as described in the embodiment illustrated in FIGS. 5 and 6. The surrounding liquid cryogen in the pressure rasing vessel keeps the vessel sufficiently cool that any exhaust gas can be condensed back to the liquid phase, instead of being wasted.

There are thus described methods and apparatus for the supply of a liquid Cryogen to, for example, a cryosurgical instrument in which problems of the freezing of valves located in the liquid cryogen line are eliminated because all control valves are located in lines in the part of the system handling gas, which is not at cryogenic temperatures. Heat gain by the liquid cryogen in the supply systems can be significantly reduced, and more flexible control of the flow rate can be achieved even at low flow rates.

The invention is particularly suitable for use in supplying liquid cryogen for cryosurgical use. However, the invention may be used in any cryogenic system where it is desired to control variably the flow rate of liquid under cryogenic conditions.

I claim:

1. Apparatus for supplying liquid cryogen, wherein the flow rate of the liquid cryogen is controlled by controlling variably the pressure of propellant gas acting directly or indirectly on the liquid cryogen.

2. Apparatus according to claim 1, comprising a liquid cryogen reservoir chamber, and means for controlling variably said pressure of propellant gas acting on the liquid cryogen in the chamber to drive the liquid from the chamber at a desired flow rate.

3. Apparatus according to claim 2, further comprising an unregulated delivery conduit along which the liquid cryogen flows from the chamber.

4. Apparatus according to claim 2, wherein the means for controlling the propellant gas pressure comprises a source of pressurised propellant gas, and control valve means coupled between the source and the liquid cryogen reservoir chamber for controlling the pressure supplied to the cryogen reservoir chamber.

5. Apparatus according to claim 4, further comprising electronic control circuit means for controlling operation of the control valve means.

6. Apparatus according to claim 5, wherein the electronic circuit means is responsive to a measured characteristic associated with the rate of flow of cryogen, or to a measured characteristic affected by the rate of flow of cryogen.

7. Apparatus according to claim 6, wherein the measured characteristic is a measured temperature.

8. Apparatus according to claim 4, wherein the source of pressurised propellant gas comprises a replaceable precharged container containing the propellant under pressure.

9. Apparatus according to claim 4, wherein the source of pressurised gas comprises a pressure raising system for generating the gas under pressure by boiling the propellant from the liquid phase.

10. Apparatus according to claim 9, wherein the pressure raising system comprises a propellant reservoir chamber for containing the propellant in the liquid phase, and a heat exchanger, the heat exchanger having an input port coupled to the propellant reservoir chamber for drawing the liquid propellant in to the heat exchanger, and an output port for delivering the propellant gas under pressure.

11. Apparatus according to claim 10, wherein the output port of the heat exchanger is coupled in parallel to the liquid cryogen reservoir chamber, and to the propellant reservoir chamber to enable a reserve of pressure to be built up in the propellant reservoir chamber.

12. Apparatus according to claim 1, wherein the control valve means comprises venting valve means for controllably venting the propellant gas from the liquid cryogen reservoir chamber.

13. Apparatus according to claim 12, wherein the venting valve means is operable to open the liquid cryogen reservoir chamber to atmospheric pressure to thereby halt the flow of liquid cryogen.

14. Apparatus according to claim 13, wherein the venting valve means is arranged to block the supply of propellant gas when the venting valve means is in an open state for venting the liquid cryogen reservoir chamber to atmospheric pressure.

15. Apparatus according to claim 4, comprising a plurality of liquid cryogen reservoir chambers each coupled by a respective control valve means to the source of pressurised propellant gas.

16. Apparatus according to claim 15, wherein each said control valve means is individually controllable to enable the flow rate from each liquid cryogen reservoir chamber to be controlled individually.

17. Apparatus according to claim 15, wherein the source of pressurised gas comprises a pressure raising system including a propellant reservoir chamber, and the liquid cryogen reservoir chambers are contained within the propellant reservoir chamber.

18. Apparatus according to claim 1, wherein the gas used as the propellant is the cryogen in the gaseous phase.

19. Apparatus for supplying a liquid cryogen to cryosurgical apparatus, the apparatus comprising means for supplying the liquid cryogen to the cryosurgical apparatus and pressure controlling means whereby the rate of flow of the cryogen to the cryosurgical apparatus can be varied, the pressure controlling means comprising means for providing a supply of gas in communication with the liquid cryogen, and means for varying the pressure of said gas, whereby to vary the rate of flow liquid cryogen to the cryosurgical apparatus.

20. Cryosurgical apparatus comprising:

a cryosurgical device to be cooled by liquid cryogen;

a supply of liquid cryogen;

a temperature probe distinct from the cryosurgical device, for producing an electronic signal indicative of temperature sensed by the probe; and electronic control means responsive to the electronic signal for controlling the rate of flow of liquid cryogen to the cryosurgical device, whereby the cooling effect in tissue can be measured and controlled.

21. Apparatus according to claim 20, wherein the control means is operable to command a change in the rate of flow in accordance with the difference between the magnitude of the sensed characteristic, and a desired target magnitude.

22. Apparatus according to claim 20, comprising an electronically actuable flow control valve for controlling the rate of flow of cryogen in response to an electronic control signal produced by the control means.

23. Apparatus according to claim 20, wherein the control circuit comprises a programmed computer processor.

24. Cryosurgical apparatus comprising apparatus as defined in claims 1.

25. A method of controlling the rate of supply of liquid cryogen for a cryogen supply, the method comprising controlling variably the pressure of propellant gas acting directly or indirectly on the liquid cryogen, to control the flow rate.

26. A method of controlling the rate of supply of liquid cryogen to cryosurgical apparatus, in which the flow of the liquid is effected by the pressure of a gas acting directly or indirectly on the liquid, the method comprising controlling the pressure of the gas whereby to control the rate of flow of the liquid.

27. A method of controlling the supply of liquid cryogen to a cryosurgical device, the method comprising:

producing an electronic temperature indicative signal from a temperature probe distinct from, and spaced from, the cryosurgical device; and controlling the rate of flow of the liquid cryogen by electronic means responsive to the signal, whereby the cooling effect can be measured and controlled.

\* \* \* \* \*